(12) United States Patent
Jawidzik

(10) Patent No.: US 10,828,121 B2
(45) Date of Patent: Nov. 10, 2020

(54) COMPOSITE FRAME SYSTEM

(71) Applicant: Alcon Research, Ltd., Fort Worth, TX (US)

(72) Inventor: Geoffrey C. Jawidzik, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/282,403

(22) Filed: Feb. 22, 2019

(65) Prior Publication Data
US 2019/0290380 A1    Sep. 26, 2019

Related U.S. Application Data

(60) Provisional application No. 62/646,696, filed on Mar. 22, 2018.

(51) Int. Cl.
*F16M 11/00* (2006.01)
*A61B 50/10* (2016.01)
*F16M 1/00* (2006.01)

(52) U.S. Cl.
CPC ............... *A61B 50/10* (2016.02); *F16M 1/00* (2013.01); *A61B 2050/105* (2016.02)

(58) Field of Classification Search
CPC .......... E04H 9/02; E04H 9/10; E04H 12/2253
See application file for complete search history.

(56) References Cited

U.S. PATENT DOCUMENTS

| 3,340,714 | A |   | 9/1967  | Pohl |
| 3,455,775 | A |   | 7/1969  | Pohl |
| 3,594,249 | A |   | 7/1971  | Mueller-tamm |
| 3,616,019 | A |   | 10/1971 | Mueller-tamm |
| 3,711,365 | A |   | 1/1973  | Pyle |
| 3,721,597 | A |   | 3/1973  | Colburn |
| 4,313,996 | A |   | 2/1982  | Newman |
| 4,455,801 | A | * | 6/1984  | Merritt ............. E04H 9/10 109/84 |
| 4,594,292 | A |   | 6/1986  | Nagai |
| 5,114,510 | A |   | 5/1992  | Wright |
| 5,137,762 | A |   | 8/1992  | Aizawa |
| 5,813,191 | A |   | 9/1998  | Gallagher |
| 6,098,829 | A |   | 8/2000  | Mchenry |
| 6,205,728 | B1 |  | 3/2001  | Sutelan |
| 6,626,445 | B2 |  | 9/2003  | Murphy |
| RE38,508  | E |   | 4/2004  | Wright |
| 7,207,079 | B2 |  | 4/2007  | Kennedy |
| 7,385,806 | B2 |  | 6/2008  | Liao |
| 7,627,995 | B1 | * | 12/2009 | Yoder ............. E04H 12/2253 248/519 |
| 7,866,675 | B2 |  | 1/2011  | Hauser |
| 8,216,658 | B2 |  | 7/2012  | Rajabali |
| 8,426,007 | B2 |  | 4/2013  | Rajabali |

(Continued)

FOREIGN PATENT DOCUMENTS

EP    0134958 B1    11/1988

*Primary Examiner* — Amy J. Sterling

(57) ABSTRACT

The present disclosure describes composite frame systems. The internal composite frame system may include at least one composite frame component including an intermediate frame element having a first side and a second side. A first plate may be positioned on the first side, and a second plate may be positioned on the second side. One or more fastener assemblies are operable to couple the first and second plates to the intermediate frame element.

18 Claims, 11 Drawing Sheets

(56) References Cited

U.S. PATENT DOCUMENTS

| | | |
|---|---|---|
| 8,851,308 B2 | 10/2014 | Raybuck |
| 8,985,716 B2 | 3/2015 | Lundrigan |
| 9,243,659 B2 | 1/2016 | Raybuck |
| 9,562,559 B2 | 2/2017 | Schomaker |
| 10,316,578 B2 | 6/2019 | Briese |
| 2004/0084197 A1 | 5/2004 | Bortz |
| 2012/0138402 A1* | 6/2012 | Choi ..................... E04H 9/02 188/381 |
| 2017/0281295 A1 | 10/2017 | Abt |
| 2018/0011965 A1 | 1/2018 | Benjamin |
| 2018/0281269 A1 | 10/2018 | Sundquist |
| 2020/0061937 A1 | 2/2020 | Matsumoto |

\* cited by examiner

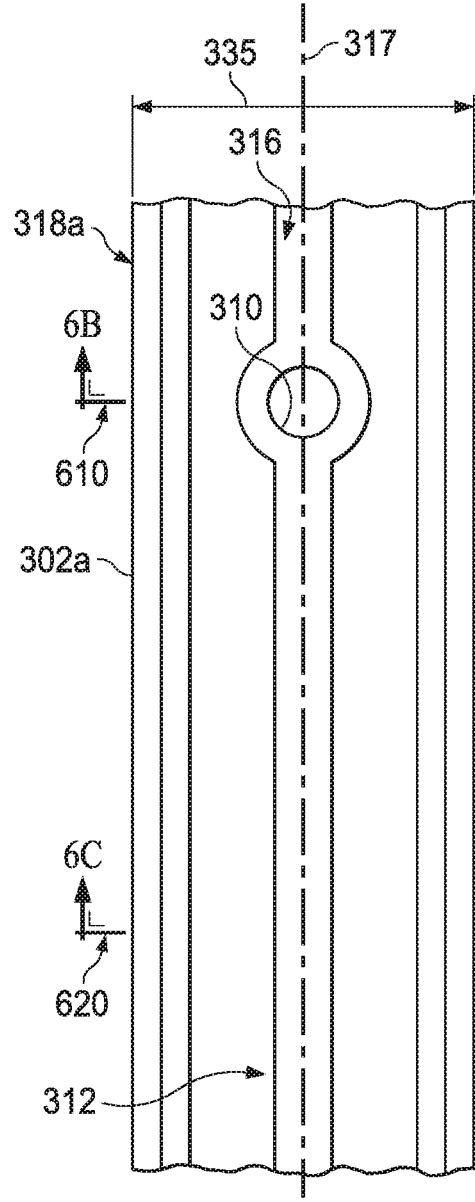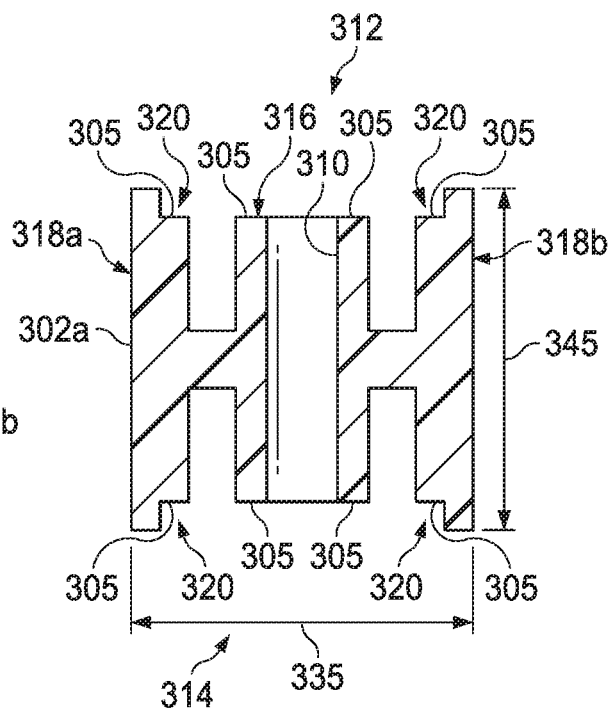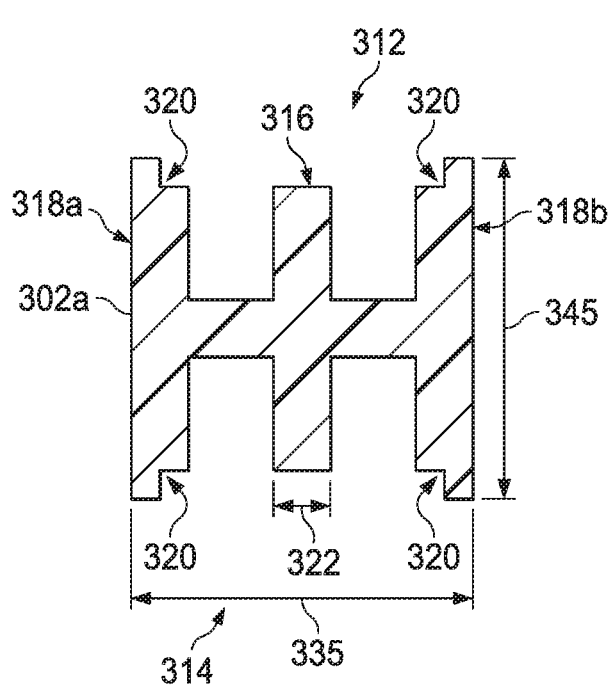
FIG. 6A
FIG. 6B
FIG. 6C

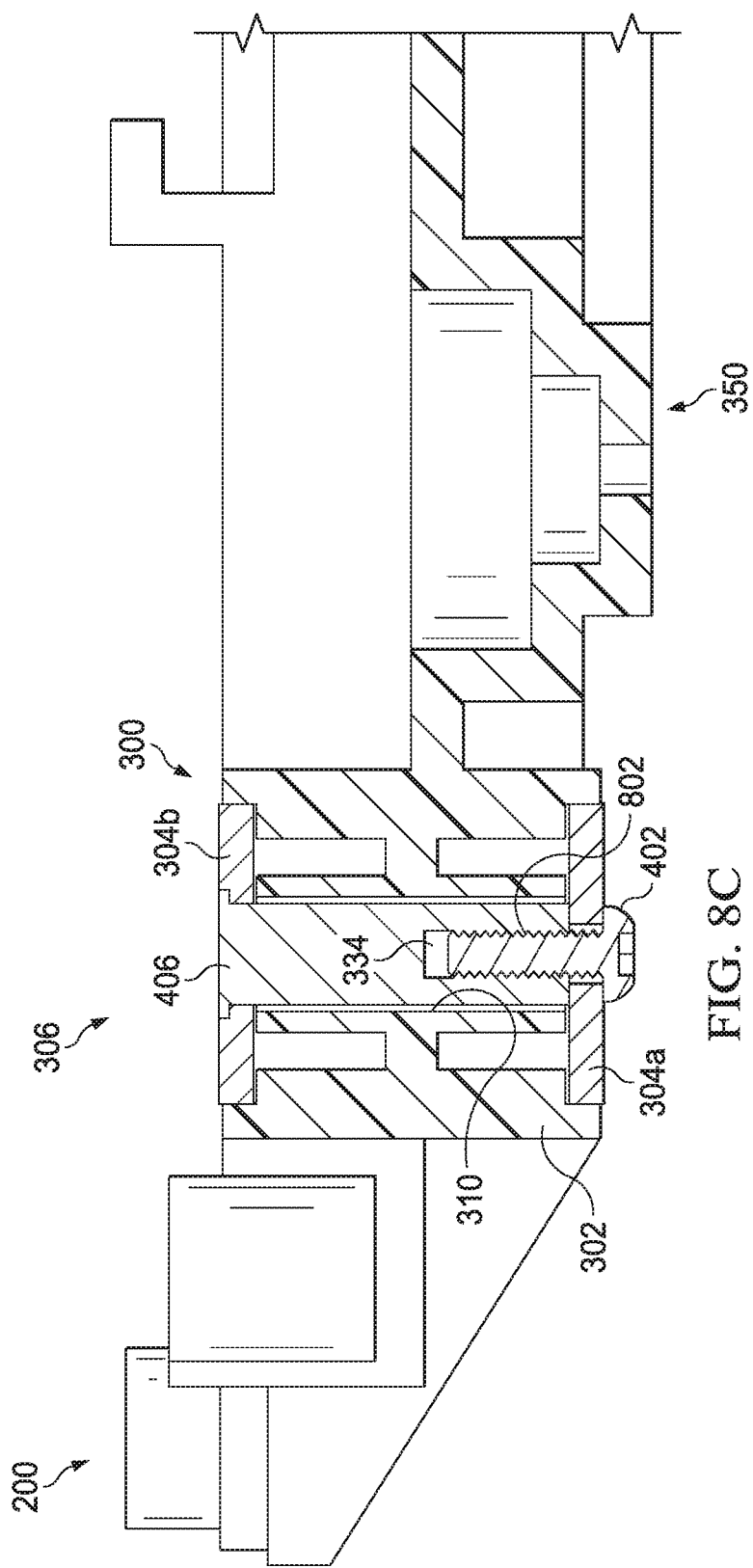

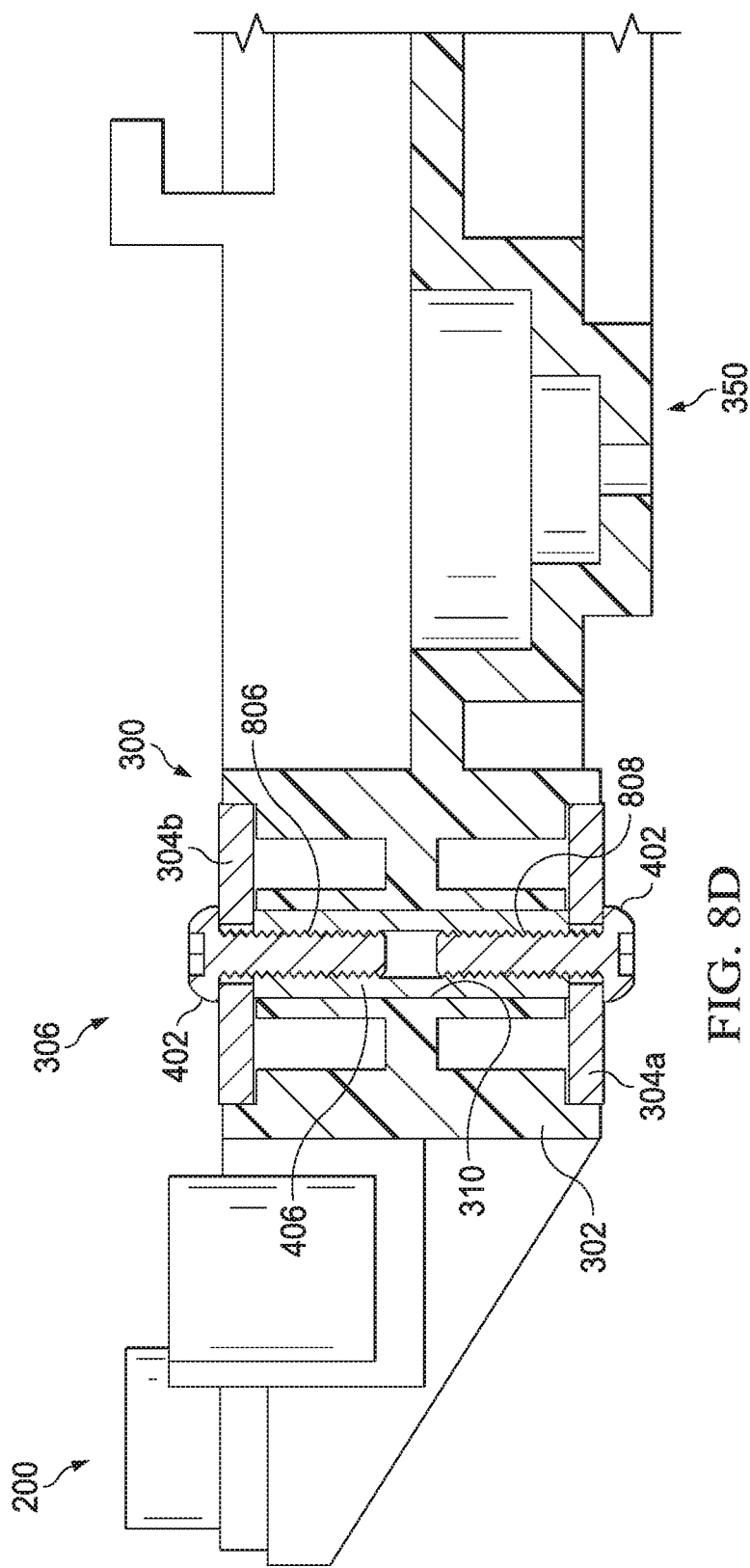

COMPOSITE FRAME SYSTEM

CROSS-REFERENCE TO RELATED APPLICATIONS

This application claims the benefit of U.S. Provisional Application No. 62/646,696, filed Mar. 22, 2018, the entire contents of which are incorporated herein by reference.

TECHNICAL FIELD

The present disclosure generally pertains to support structures. More particularly, but not by way of limitation, the present disclosure pertains to support structures for surgical consoles.

BACKGROUND

Various support structures for the storage and transportation of surgical consoles have been used in the past. Simple, open support structures with several stacked shelves are sometimes used. The support structures may be made from metal or plastic and may employ solid shelves or shelves formed from spaced, parallel members. Such support structures may not be specifically designed for the surgical console they serve, and may provide little, if any, protection for the ancillary equipment and consumables that are used with the surgical console.

SUMMARY

A first aspect of the present disclosure is directed to a composite frame system. The composite frame system includes at least one frame member that includes an intermediate frame element having a first side and a second side disposed opposite the first side; a first plate positioned on the first side of the intermediate frame element; a second plate positioned on the second side of the intermediate frame element; and at least one fastener assembly extending through the first plate, the intermediate frame element, and the second plate and attaching the first plate and the second plate to the intermediate frame element.

The intermediate frame element may include a main web and at least one outer web. The at least one outer web may extend along a length of the intermediate frame element in an orientation parallel to a longitudinal axis of the intermediate frame element. At least a portion of the main web may extend at an angle relative to the at least one outer web such that the main web forms a zigzag pattern along a length of the intermediate frame element. The intermediate frame element may include a main web and an overall width. The main web may have a width that is between 5% and 35% of the overall width. The intermediate frame element may have an overall depth, and the first plate and the second plate may each have a thickness between 5% and 15% of the overall depth. The at least one fastener assembly may include a male fastener and a female fastener. The at least one fastener assembly may include at least one male fastener and a standoff. The at least one fastener assembly may include a male fastener, a standoff, and a female fastener. The at least one fastener assembly may apply a compressive force to the intermediate frame element, the first plate, and the second plate. A compressive force applied by the at least one fastener assembly may not be transmitted through the intermediate frame element. The intermediate frame element may be made from a first material, and the first plate and the second plate may be made from a second material different from the first material. The first material may have a lower yield strength than the second material. The first material may include a plastic, and the second material may include a metal. The composite frame system may include at least one structural cross-member integrally formed with the intermediate frame element. The at least one fastener assembly may include a plurality of fastener assemblies, and a distance may separate each of the plurality of fastener assemblies. The distance may be between two inches and six inches.

A second aspect of the present disclosure is directed to a surgical console that may include a surgical console base; a surgical tray mounted on the surgical console base; a work surface mounted on the surgical console base; a display screen mounted on the surgical console base; a surgical instrument panel mounted on the surgical console base; a computer subsystem mounted within the surgical console base; and a fluidics subsystem mounted within the surgical console base. The console base may include a composite frame system. The composite frame system may include at least one frame member that includes an intermediate frame element having a first side and a second side disposed opposite the first side; a first plate positioned on the first side of the intermediate frame element; a second plate positioned on the second side of the intermediate frame element; and at least one fastener assembly extending through the first plate, the intermediate frame element, and the second plate and attaching the first plate and the second plate to the intermediate frame element. The computer subsystem may be mounted to the at least one structural cross-member within the surgical console base. The fluidics subsystem is mounted to the at least one structural cross-member within the surgical console base.

BRIEF DESCRIPTION OF THE DRAWINGS

For a more complete understanding of the present disclosure and the associated features and advantages described herein, reference is now made to the following description, taken in conjunction with the accompanying drawings, which are not to scale, in which like numerals refer to like features, and in which:

FIGS. 6A, 6B, and 6C are various detail and cross-sectional views of the example intermediate frame element depicted in FIG. 4;

FIGS. 8A, 8B, 8C, and 8D are each a cross-sectional view of the example composite frame component depicted in FIG. 2 and FIG. 3 including various example fastener assemblies.

DETAILED DESCRIPTION

Figure 1:
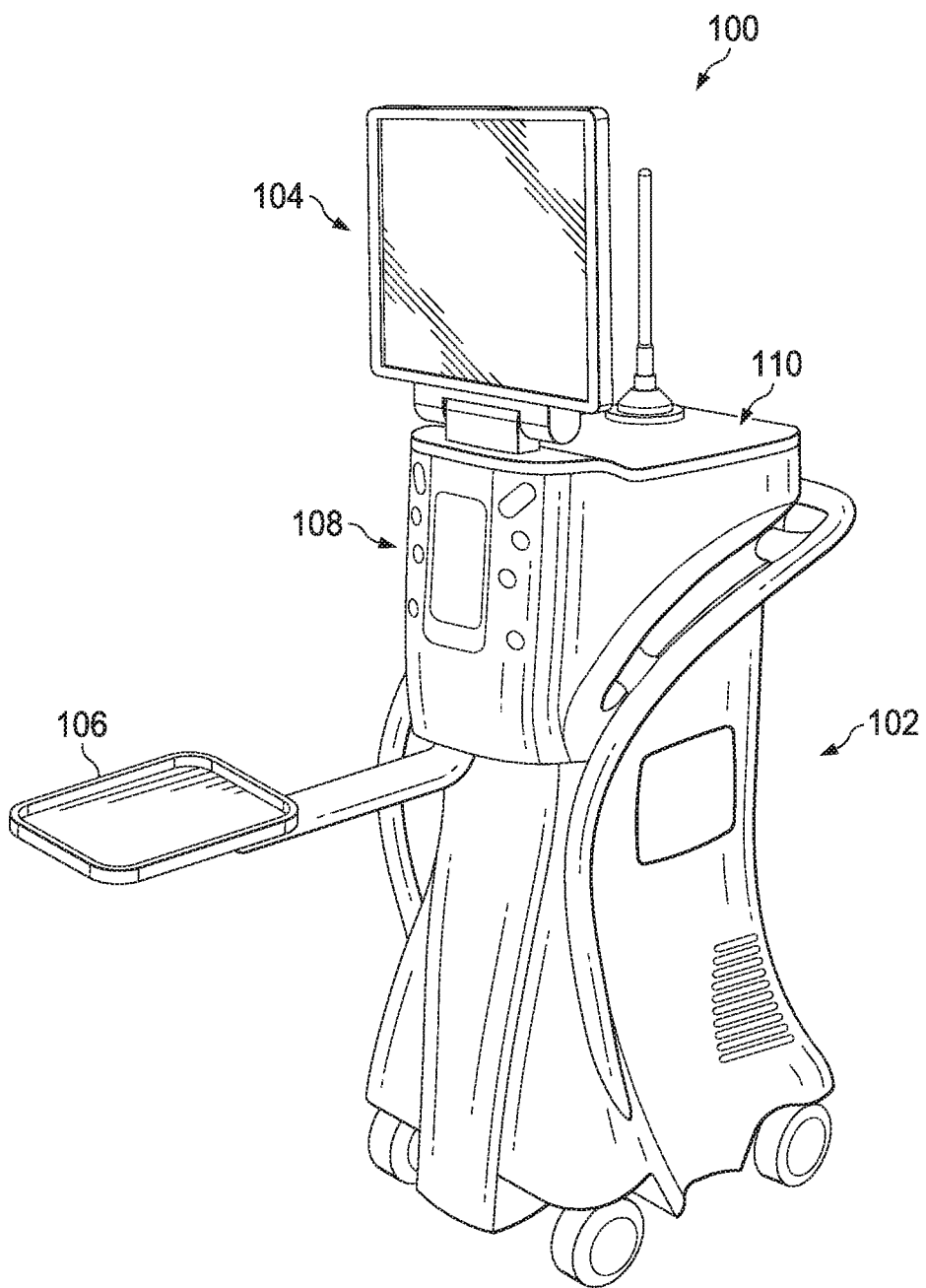
FIG. 1 is a perspective view of an example surgical console similar to the CENTURION® VISION SYSTEM produced by Alcon Laboratories, Inc., located at 6201 South Freeway, Fort Worth, Tex. 76134.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The disclosed composite frame systems may improve the manufacturability of frame systems and surgical consoles including internal frame systems by allowing for efficient strengthening and/or stiffening of the frame system through the selective, limited use of strong, rigid material, e.g., sheet metal. This type of frame construction avoids issues with previous structural frames including relatively high mass density (metal frames), structural weakness and creep or cold flow (plastic frames), and high cost (structural frames using laminate composite materials and space structures). A composite frame system of the present disclosure may be manufactured through a less difficult fabrication process that is more cost-effective and uses materials more efficiently than fabrication processes for previous structural frames. In addition, composite frame systems of the present disclosure may improve manufacturability of frame systems while still providing adequate strength and/or durability without increasing the overall size and/or weight of the frame system. Although the present disclosure is made in the context of frame systems for surgical consoles, the scope of the disclosure is not limited to surgical consoles. Rather, the present disclosure is applicable to other instances in which a frame system is needed or desired.

According to some implementations, systems of the present disclosure typically include at least one composite frame component including an intermediate frame element and a first plate and a second plate. The first plate and the second plate are attached to the intermediate frame element on opposing sides with at least one fastener assembly. The composite frame component may be assembled or incorporated into a novel composite frame system that provides strength and rigidity at a lower cost and through a less difficult fabrication process. Example systems and components are described in greater detail in FIG. 1 through FIG. 8. However, aspects of these systems and components may be combined with one another and with systems and components otherwise described herein, but not illustrated in the figures.

FIG. 1 illustrates an example surgical console 100 similar to the CENTURION® VISION SYSTEM produced by Alcon Laboratories, Inc., located at 6201 South Freeway, Fort Worth, Tex. 76134. The surgical console 100 may include a surgical console base 102, a display screen 104, a surgical tray 106, a surgical instrument panel 108, and a work surface 110. However, the scope of the disclosure is not so limited. The surgical console 100 is intended to encompass other components or features even though not expressly depicted in FIG. 1 or described in detail below.

The surgical console base 102 may house various subsystems that operate to perform a surgical procedure. For example, these subsystems may include a computer subsystem 210 and/or a fluidics subsystem 206, as described in more detail below with reference to FIG. 2. The surgical console base 102 may also include various structural systems that provide support for the surgical console base 102 and/or other components of the surgical console 100. For example, these structural systems may include an internal composite frame system 200, component-mounting systems 202 and 204, a storage system 208, and at least one composite frame component 300, as described in more detail below with reference to FIG. 2.

The display screen 104 may show data relating to system operation and performance during a surgical procedure and may be associated with the computer subsystem 210. In some implementations, the display screen 104 may be a touch-screen display. The display screen 104 may be physically coupled to the surgical console base 102 by way of the component-mounting system 204, as described in more detail below in reference to FIG. 2. In some implementations, the display screen 104 may be adjustable. For example, the display screen 104 may be operable to swivel and/or tilt to allow for improved visibility during a surgical procedure.

The surgical instrument panel 108 may provide attachment points for various surgical instruments used during a surgical procedure. Depending on the surgical procedure being performed, these surgical instruments may include, e.g., vitrectomy hand pieces, aspirators, illuminators, infusion cannulas, irrigators, ultrasonic oscillation hand pieces, and/or other surgical instruments or tools. The surgical instrument panel 108 may also be fluidically, physically, and/or electronically coupled to the various subsystems and structural systems housed in the surgical console base 102, as described above. For example, the surgical instrument panel 108 may be fluidically coupled to the fluidics subsystem 206, electronically coupled to the computer subsystem 210, and/or physically coupled to the internal composite frame system 200, the composite frame component 300, and/or a component-mounting system, as described in more detail below in reference to FIG. 2.

The surgical tray 106 may be designed to hold surgical equipment, tools, supplies, or other items including, but not limited to, patient files or other documents, during a surgical procedure. The surgical tray 106 may be physically coupled to the surgical console base 102 by way of the internal composite frame system 200, the composite frame component 300, and/or a component-mounting system, as described in more detail below in reference to FIG. 2. In some implementations, the surgical tray 106 may be adjustable. For example, the surgical tray 106 may be operable to be raised and lowered to account for the height preference of a user during a surgical procedure. The surgical tray 106 may also be operable to extend away from the surgical console 100 or move laterally to either side of the surgical console 100 as needed during a surgical procedure. In other implementations, the surgical tray 106 may be operable to be collapsed and stored within or up against the surgical console base 102.

The work surface 110 may be similarly designed to hold surgical equipment, tools, supplies, or other items including, but not limited to, patient files or other documents, during a surgical procedure. The work surface 110 may be physically coupled to the surgical console base 102 by way of the component-mounting system 202, as described in more detail below in reference to FIG. 2. In some implementations, the work surface 110 may be similarly adjustable, as described above with reference to the surgical tray 106. The work surface 110 may also be operable to rotate or extend away from the surgical console 100.

As depicted in FIG. 1, the various components of the surgical console 100 are illustrated in a specific configuration and orientation in relation to one another. For example, the surgical instrument panel 108 and the surgical tray 106 are depicted as being mounted to a front side of the surgical console base 102. For further example, the display screen 104 and the work surface 110 are depicted as being mounted to a top side of the surgical console base 102. However, the scope of the disclosure is not so limited. The surgical console 100 is intended to encompass components in other configurations or orientations even though not expressly depicted in FIG. 1.

Figure 2:
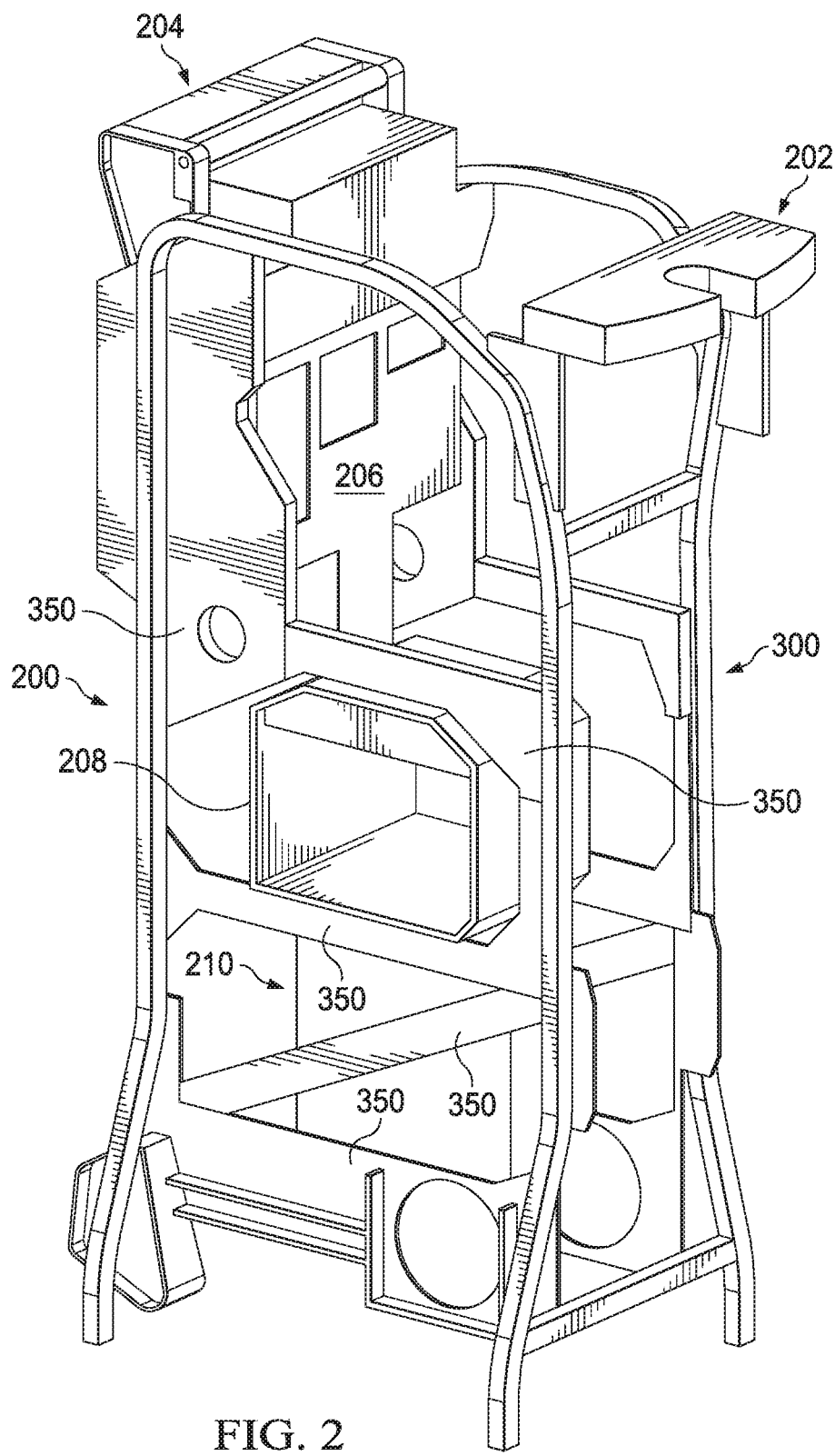
FIG. 2 is a perspective view of an example internal composite frame system that may be used with the surgical console depicted in FIG. 1.

FIG. 2 illustrates an example internal composite frame system 200 that includes at least one composite frame component 300 to support various loads throughout the internal composite frame system 200. In some implementations, the internal composite frame system 200 may be included in a surgical console, e.g., the surgical console 100 described above with reference to FIG. 1. In some implementations, components of a surgical system, e.g., an ophthalmic surgical system, may be coupled to the internal composite frame system 200. For example, FIG. 2 depicts the fluidics subsystem 206 and the computer subsystem 210 coupled to the internal composite frame system 200. The internal composite frame system 200 may also include various structural systems that provide support for a surgical console, e.g., the surgical console 100. For example, FIG. 2 depicts the component-mounting systems 202 and 204 and the storage system 208 as included in the internal composite frame system 200.

The composite frame component 300 is described in more detail below with reference to FIG. 3 through FIG. 8. In general, the composite frame component 300 may include a novel configuration of components that provide strength and rigidity to the internal composite frame system 200 at a lower cost and through a less difficult fabrication process. In some implementations, a single, continuous composite frame component 300 may be formed in a predetermined shape that defines the structural shape of the internal composite frame system 200. In other implementations, multiple composite frame components 300 may be formed separately and subsequently coupled into a predetermined shape that defines the structural shape of the internal composite frame system 200. The internal composite frame system 200 may include at least one structural cross-member 350. In some implementations, the structural cross-member 350 may be integrally formed with the composite frame component 300 or a component thereof. In other implementations, the structural cross-member 350 may be separately formed and subsequently coupled to the composite frame component 300. In some implementations, the structural cross-member 350 may increase the strength of the internal composite frame system 200. In other implementations, the structural cross-member 350 may provide mounting points, e.g., shelves, sidewalls, compartments, etc., for components of the internal composite frame system 200 or a surgical console, e.g., the surgical console 100. For example, FIG. 2 depicts the component-mounting systems 202 and 204, the fluidics subsystem 206, the storage system 208, and the computer subsystem 210 mounted to the structural cross-members 350. FIG. 2 depicts the composite frame component 300 with an example structural shape and the internal composite frame system 200 with an example configuration of the structural cross-members 350. However, the scope of the disclosure is not so limited. The internal composite frame system 200 is intended to encompass components in other configurations even though not expressly depicted in FIG. 2.

The component-mounting systems 202 and 204 may be designed to support various components of a surgical console, e.g., the surgical console 100. For example, the component-mounting systems 202 and 204 may be designed to support the display screen 104, the surgical tray 106, or the work surface 110, as described above with reference to FIG. 1. The component-mounting systems 202 and 204 may be designed to physically couple components to and transfer loads to the internal composite frame system 200 and/or the composite frame component 300. In some implementations, the component-mounting system 202 may be similar to the component-mounting system 204. In other implementations, the component-mounting system 202 may be customized to accommodate a specific type of component, while the component-mounting system 204 may be customized to accommodate a different type of component. For example, the component-mounting system 202 may be specifically designed to support and mount the work surface 110, while the component-mounting system 204 may be specifically designed to mount and support the display screen 104. FIG. 2 depicts the internal composite frame system 200 with two component-mounting systems 202 and 204. However, the scope of the disclosure is not so limited. The internal composite frame system 200 is intended to encompass systems with more or fewer component-mounting systems that may be arranged in different configurations or orientations even though not expressly depicted in FIG. 2.

In some implementations, the component-mounting systems 202 and 204 may be formed using a variety of techniques, e.g., insert molding, injection molding, gas-assist injection molding, metal injection molding, Thixo-molding, compression molding, hand layup, cast molding, machining, welding, pultruding, extruding, hydroforming, mechanical bending, die forming, or another suitable technique.

The fluidics subsystem 206 may be configured to perform various surgical procedures. The fluidics subsystem 206 may be physically and/or fluidically coupled to the surgical instrument panel 108. The fluidics subsystem 206 may be electronically coupled to the computer subsystem 210. The fluidics subsystem 206 may be physically coupled to the internal composite frame system 200, the composite frame component 300, the structural cross-member 350, and/or a component-mounting system (not expressly shown). In some implementations, the structural cross-member 350 may be designed specifically as a shelf, compartment, or other mounting feature to accommodate the fluidics subsystem 206. In some implementations, the fluidics subsystem 206 may include an irrigation system and an aspiration system that deliver fluid to and aspirate fluid from a surgical site, e.g., a patient's eye, by way of the surgical instrument panel 108 and the connected surgical instruments. For example, the fluidics subsystem 206 may be configured to operate various pneumatic surgical tools or instruments, e.g., pneumatic vitrectomy hand pieces or probes, irrigators, aspirators, etc. The irrigation system and/or the aspiration system may include various cassettes, tubing systems, reservoirs, sensors, pumps, vents, etc.

The computer subsystem 210 may be configured to perform various surgical procedures. The computer subsystem 210 may be electronically coupled to the surgical instrument panel 108, the fluidics subsystem 206, the display screen 104, and/or other components of the surgical console 100. The computer subsystem 210 may be physically coupled to the internal composite frame system 200, the composite frame component 300, the structural cross-member 350, and/or a component-mounting system (not expressly shown). In some implementations, the structural cross-member 350 may be designed specifically as a shelf, compartment, or other mounting feature to accommodate the computer subsystem 210. In some implementations, the computer subsystem 210 may include one or more processors. The processor may include a single processing device or a plurality of processing devices. Such processing device may be a microprocessor, a controller (which may be a micro-controller), a digital signal processor, a microcomputer, a central processing unit, a field programmable gate array, a programmable logic device, a state machine, logic circuitry, control circuitry, analog circuitry, digital circuitry, and/or any device that manipulates signals (analog and/or digital) based on operational instructions. In some implementations, the computer subsystem 210 may include a memory coupled to and/or embedded in the processors. The memory may be a single memory device or a plurality of memory devices. Such memory device may be a read-only memory, a random access memory, a volatile memory, a non-volatile memory, a static memory, a dynamic memory, a flash memory, a cache memory, and/or any device that stores digital information. Note that when the processors implement one or more functions via a state machine, analog circuitry, digital circuitry, and/or logic circuitry, the memory storing the corresponding operational instructions may be embedded within, or external to, the circuitry comprising the state machine, the analog circuitry, the digital circuitry, and/or the logic circuitry. The memory may store, and the processor may execute, operational instructions. The fluidics subsystem 206 and the computer subsystem 210 may overlap and cooperate to perform various aspects of a surgical procedure.

Figure 3:
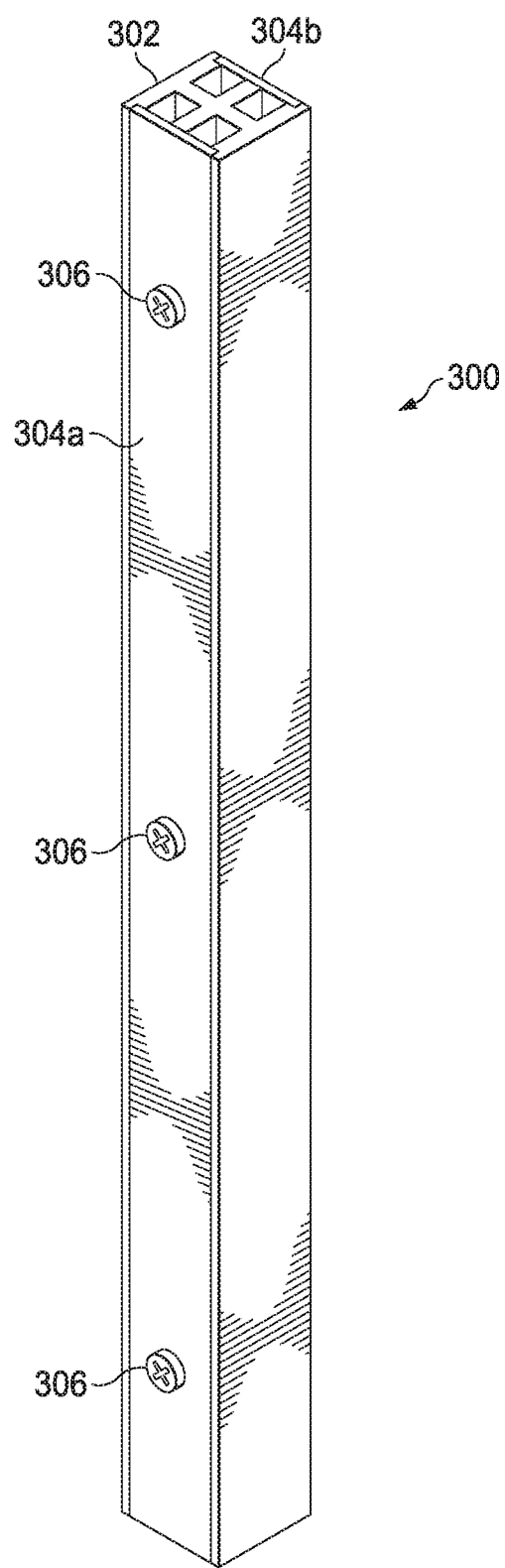
FIG. 3 is a perspective view of an example composite frame component.

FIG. 3 illustrates an example composite frame component 300 that may be included in the internal composite frame system 200. As depicted in FIG. 3, the example composite frame component 300 is relatively short and straight. The example composite frame component 300 also does not include the structural cross-member 350. However, the scope of the disclosure is not so limited. The composite frame component 300 may be formed at various lengths and in various predetermined shapes. The composite frame component 300 may also include one or more of the structural cross-members 350. For example, the composite frame component 300, as depicted in FIG. 2, is formed in a long, curved shape and includes a number of structural cross-members 350.

The composite frame component 300 includes an intermediate frame element 302, a first plate 304a, a second plate 304b, and a plurality of fastener assemblies 306. In general, the composite frame component 300 may be fabricated more easily and at a lower cost than previous structural frame systems. As described above with reference to FIG. 2, the composite frame component 300 provides structural shape and/or support to the internal composite frame system 200, the surgical console 100, and the components thereof. The composite frame component 300 may be configured such that the first plate 304a and the second plate 304b bear the majority of the loads exerted on the composite frame component 300. The intermediate frame element 302 may bear the remaining portions of the loads and maintain a separation between the first plate 304a and the second plate 304b. The fastener assemblies 306 attach and maintain the position of the first plate 304a and the second plate 304b with respect to the intermediate frame element 302. The first plate 304a, the second plate 304b, and the fastener assembly 306, as depicted in FIG. 3, provide the composite frame component 300 with structural and mechanical properties similar to those of an I-beam, an H-beam, a W-beam, a rolled steel joist, or a double-T. The first plate 304a and the second plate 304b act in a similar fashion to the flanges of an I-beam. The fastener assembly 306 act in a similar fashion to the web of an I-beam. For example, just as the web of an I-beam resists shear forces, the fastener assembly 306 resist shear forces that may be exerted on the composite frame component 300. For further example, just as the flanges of an I-beam resist bending moments, the first plate 304a and the second plate 304b resist bending moments that may be exerted on the composite frame component 300. The intermediate frame element 302, the first plate 304a, and the second plate 304b are described in more detail below with reference to FIG. 4 and FIG. 5. Although a portion of the fastener assemblies 306 are shown extending beyond the first plate 304a, the ends of the fastener assemblies 306 may be flush with the exterior surface of one or both of the first plate 304a and the second plate 304b, as shown, for example, in FIG. 8B.

In some implementations, the intermediate frame element 302 may be in the form of a slender beam having a variety of cross-sectional shapes and may be made of a first material while the first plate 304a and the second plate 304b may be made of a second material. In some implementations, the first material may be less dense, more flexible (e.g., the first material may have a lower modulus of elasticity), and weaker (e.g., the first material may have a lower yield strength) than the second material. For example, in some instances, the first material may be a plastic, while the second material may be a metal. In some implementations, the first material may be polyamide, polyphenylene sulfide, polycarbonate, polyvinylchloride, polyarylate, polysurfone, acetal, cellulosics, polyester, melamine, phenolic, urea molding compound, vinyl ester, unsaturated polyester, PC/ABS (polycarbonate/acrylonitrile butadiene styrene), polyetheretherkeytone, liquid crystal polymer, polypropylene, high density polyethylene, bulk molding compound, sheet molding compound, epoxy, or polyurethane. In some implementations, material fillers such as carbon or glass fibers may be added to the first material. In further implementations, the second material may be sheet metal, aluminum, aluminum alloy, steel, carbon fiber, ceramic, polymers, and/or composite materials. Other materials may also be used.

In some implementations, the first plate 304a, the second plate 304b, and the intermediate frame element 302 may be formed using a variety of techniques, e.g., insert molding, injection molding, gas-assist injection molding, metal injection molding, Thixomolding, compression molding, hand layup, cast molding, machining, welding, pultruding, extruding, hydroforming, mechanical bending, die forming, or another technique.

In some implementations, the fastener assembly 306 may include, for example, male fasteners, female fasteners, deformable fasteners, and/or standoffs. For example, male fasteners may include, but are not limited to, bolts or screws with flat-heads, button-heads, socket-heads, and pan-heads. Female fasteners may include, but are not limited to, threaded clinch nuts and hex nuts, and deformable fasteners may include, but are not limited to, rivets. For further example, standoffs may include, but are not limited to, threaded clinch standoffs and threaded standoffs. Various examples of the fastener assemblies 306 are depicted and described in more detail below with reference to FIG. 8A through FIG. 8D. These described examples are not intended to be limited, however. Consequently, other fastener assemblies are intended to be encompassed within the scope of the present disclosure.

Figure 4:
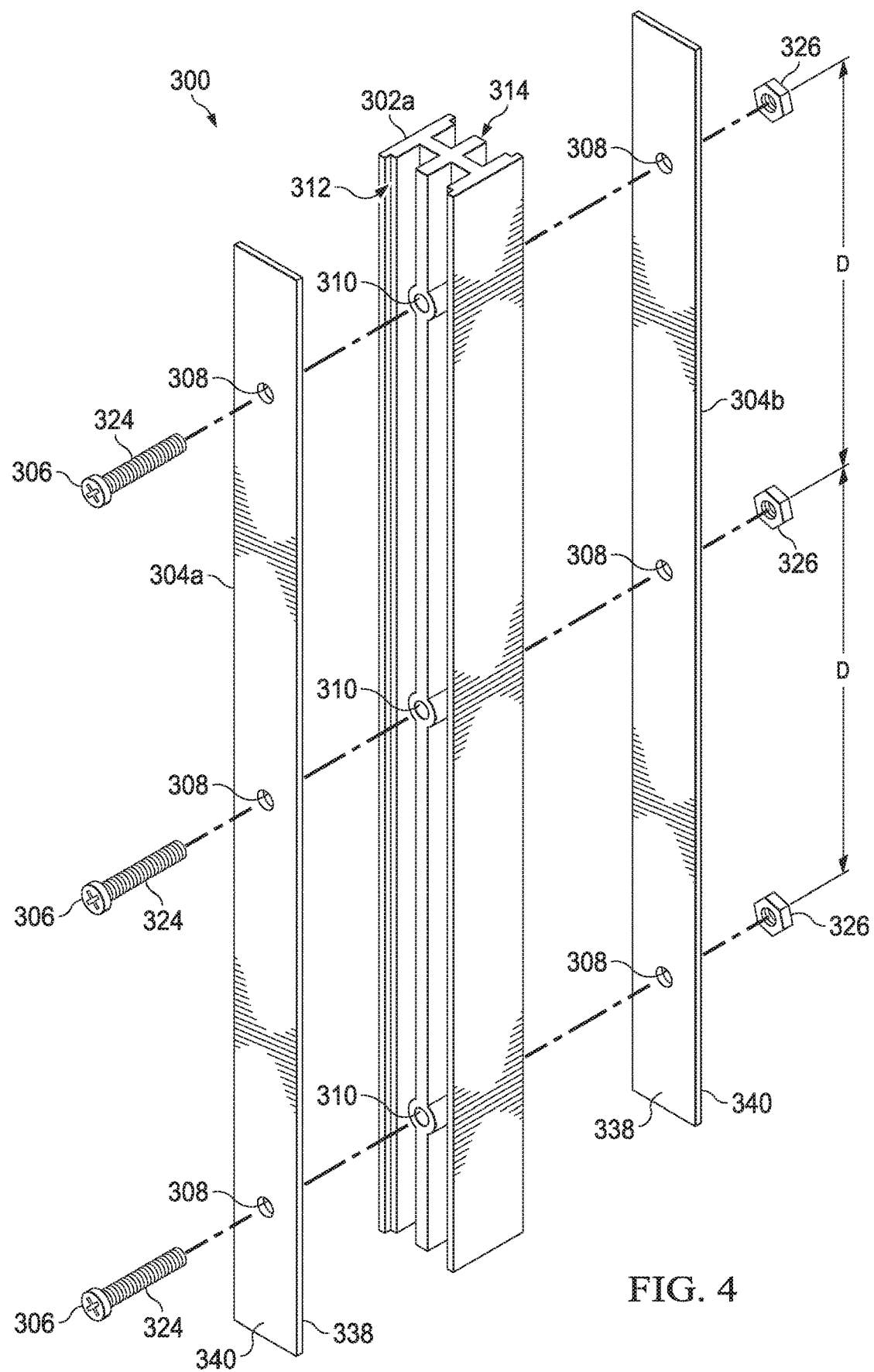
FIG. 4 is an exploded view of the example composite frame component depicted in FIG. 3 including an example intermediate frame element.

FIG. 4 illustrates an exploded view of the composite frame component 300 with an example intermediate frame element 302a. The intermediate frame element 302a is described in more detail below with reference to FIGS. 6A, 6B, and 6C. Referring again to FIG. 4, the intermediate frame element 302a includes a plurality of fastener through-holes 310. The intermediate frame element 302a also includes a first side 312 and a second side 314 opposite the first side 312. The intermediate frame element 302a is configured such that the first plate 304a attaches to the first side 312, and the second plate 304b attaches to the second side 314. The first plate 304a includes a plurality of fastener through-holes 308. The plurality of fastener through-holes 308 align with and have a size corresponding to the plurality of fastener through-holes 310 formed in the intermediate frame element 302a. The second plate 304b includes a plurality of fastener through-holes 308. Similar to the first plate 304a, the plurality of fastener through-holes 308 formed in the second plate 304b align with and have a size corresponding to the plurality of fastener through-holes formed in the intermediate frame element 302a.

In some implementations, the second plate 304b may include features that are identical to those of the first plate 304a. In other implementations, the second plate 304b may be have features reversibly arranged with respect to the first plate 304a, or features of the second plate 304b may be mirrored with respect to the first plate 304a. In further implementations, the first plate 304a and the second plate 304b may be designed with differing features to accommodate the shape of the composite frame component 300.

Referring again to FIG. 4, The plurality of fastener through-holes 308 formed in the first plate 304a and the second plate 304b and the plurality of fastener through-holes 310 formed in the intermediate frame element 302a are configured to accommodate the fastener assemblies 306 such that the fastener assemblies 306 may pass through the fastener through-holes 308 in the first plate 304a, the fastener through-holes 310 in the intermediate frame element 302a, and the fastener through-holes 308 in the second plate 304b.

Figure 5:
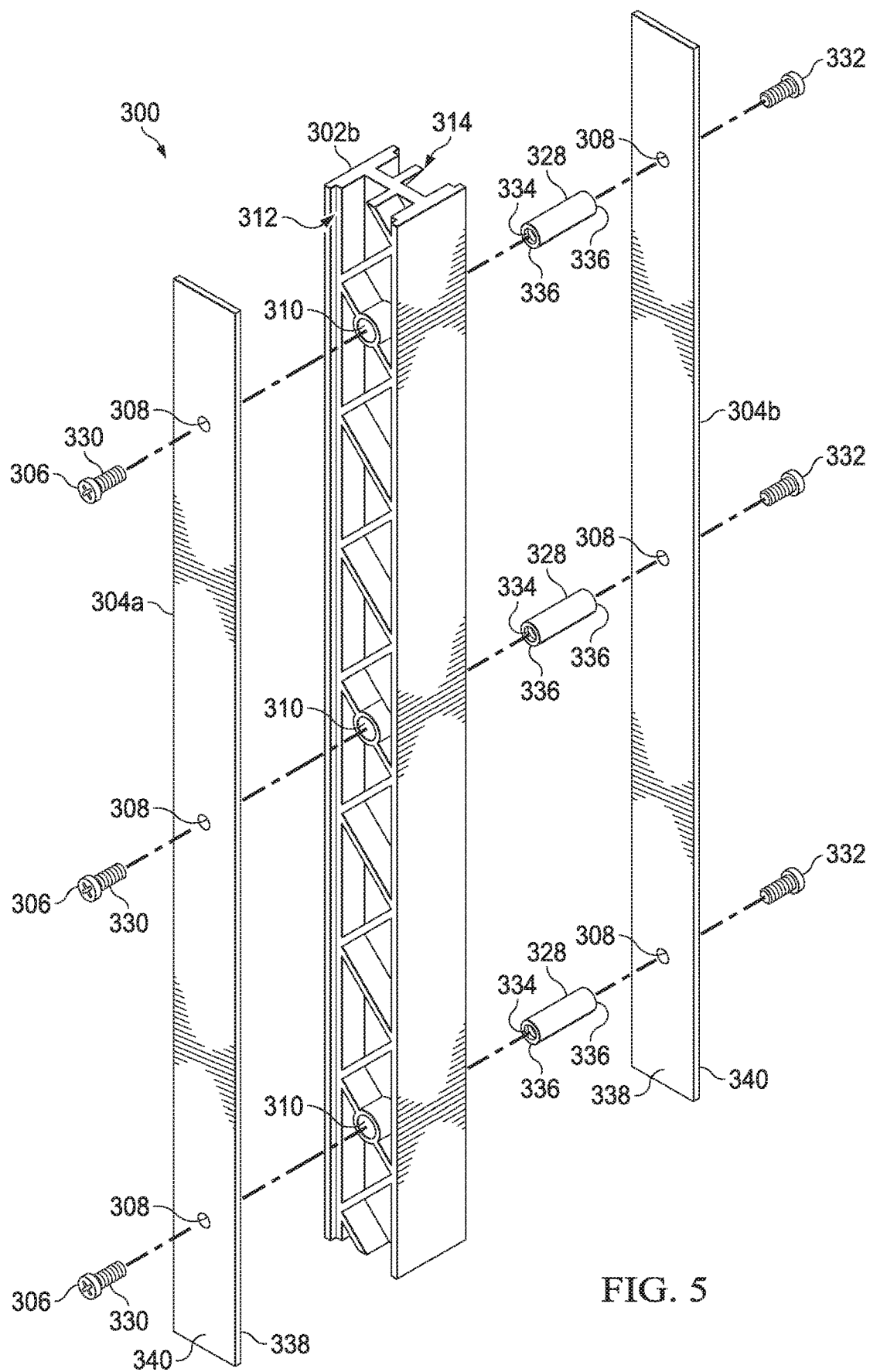
FIG. 5 is an exploded view of the example composite frame component depicted in FIG. 3 including another example intermediate frame element.

As depicted in FIG. 4, the fastener assemblies 306 include a male fastener 324 and a female fastener 326, and the intermediate frame element 302a includes the plurality of fastener through-holes 310 with a diameter sized to accommodate the male fasteners 324. In the illustrated example, the male fastener 324 and the female fastener 326 include corresponding threads so as to form a threaded connection when coupled to each other. When the male fastener 324 and the female fastener 326 are coupled together, the male and female fasteners 324 and 326 securely sandwich the intermediate frame component 300 between the first plate 304a and the second plate 304b. However, the scope of the disclosure is not so limited. The composite frame component 300 and the intermediate frame element 302a are intended to encompass other configurations that may include other fasteners and differently designed features. For example, in some implementations, the intermediate frame element 302a may be configured to include the plurality of fastener through-holes 310 with a diameter sized to accommodate the fastener assemblies 306 having different shapes, sizes, or configurations. As shown in FIG. 5 and discussed in more detail below, for example, the fastener assemblies 306 include a standoff 328 that pass through at least the fastener through-holes 310 formed in the intermediate frame element 302a.

As depicted in FIG. 4, adjacent through-holes 308, fastener assemblies 306, and fastener through-holes 310 are separated by a uniform distance D. In some implementations, the distance D may be between three inches and five inches, particularly when used with a surgical console, e.g., the surgical console 100. However, the scope of the disclosure is not so limited. In other instances, the distance D may be greater than five inches or less than three inches. Further, in some implementations, the distance between adjacent fastener through-holes 308 may not be uniform but, rather, may vary along a length of the composite frame component 300. In general, the strength and rigidity of the composite frame component 300 and the internal composite frame system 200 may increase as the distance between each of the plurality of fastener through-holes 308 decreases. Likewise, in general, the strength and rigidity of the composite frame component 300 and the associated internal composite frame system 200 may decrease as the distance between adjacent fastener through-holes 308 increases.

FIG. 5 illustrates an exploded view of the composite frame component 300 with another example intermediate frame component 302b. The composite frame components 300 depicted in FIG. 4 and FIG. 5 include similar components but differ in that the intermediate frame elements 302a and 302b and the example fastener assemblies 306 depicted respectively therein are different. As depicted in FIG. 5, the intermediate frame element 302b includes a cross-sectional structure that is different from the cross-sectional structure of the intermediate frame element 302a depicted in FIG. 4. The intermediate frame element 302b is described in more detail below with reference to FIGS. 7A, 7B, 7C, and 7D.

As shown in FIG. 5, the fastener assemblies 306 include a first male fastener 330, a second male fastener 332, and the standoff 328. In the illustrated example, the standoff 328 defines a threaded bore 334 that receives the first and second male fasteners 330 and 332 so as to form a threaded connection and secure the first plate 304a, the intermediate frame element 302a, and the second plate 304b together. The intermediate frame element 302b includes a plurality of fastener through-holes 310 sized to accommodate the standoff 328. In some instance, a cross-sectional size (e.g., diameter) of the fastener through-hole 310 that is configured to accommodate a standoff may be larger than a cross-sectional size (e.g., diameter) of a fastener through-hole 310 that is not configured to accommodate a standoff. However, the scope of the disclosure is not so limited. The composite frame component 300 and the intermediate frame element 302b are intended to encompass other configurations that may include other fasteners and differently designed features. For example, the intermediate frame element 302b may be designed to include fastener through-holes 310 that accommodate the fastener assemblies 306 depicted in FIG. 4, which include a male fastener and a female fastener, and do not include a standoff. In some instances, the cross-sectional size (e.g., diameter) of the fastener through-hole 310 configured to accept the male and female fasteners 324 and 326 as shown in FIG. 4 may be smaller than a cross-sectional size (e.g., diameter) of the fastener through-hole 310 configured to accept a standoff, such as standoff 328, as shown in FIG. 5.

With continued reference to FIG. 5, a cross-sectional size (e.g., diameter) of the fastener through-holes 308 may be smaller than the cross-sectional size (e.g., diameter) of the fastener through-holes 310. This difference in sizes results from the standoff 328 being receivable into the fastener through-holes 310 but not receivable into the fastener through-holes 308. As explained above, the first and second male fasteners 330 and 332 are received into the threaded bore 334 formed in the standoff 328 to form a threaded connection. Further, with the construction shown in FIG. 5, end faces 336 of the standoff 328 abut surfaces 338 of the first and second plates 304a and 304b that are adjacent to the intermediate frame element 302b. In some instances, with such a construction, clamping forces provided by the male fasteners 330 and 332 are transmitted exclusively through the standoff 328, thereby preventing compressive forces from being transmitted through the intermediate frame element 302b.

FIGS. 6A, 6B, and 6C illustrate various detail and section views of the intermediate frame element 302a depicted in FIG. 4. FIG. 6A illustrates a detail view of the first side 312 of the intermediate frame element 302a. The intermediate frame element 302a is depicted with the fastener through-hole 310, as described above with reference to FIGS. 3 and 4. The intermediate frame element 302a includes a main web 316 and at least one outer web 318. As depicted in FIGS. 6A, 6B, and 6C, the intermediate frame element 302a includes an outer web 318a and an outer web 318b. However, the scope of the disclosure is not so limited. The intermediate frame element 302a is intended to encompass frame elements with other cross-sectional shapes including cross-sectional shapes with more or fewer webs.

As depicted in FIG. 6A, the main web 316 extends along the intermediate frame element 302a in a direction parallel to a longitudinal axis 317 of the intermediate frame element 302a. The outer webs 318a and 318b extend parallel to one the main web 316 along a length 325 of the intermediate frame element 302a. Thus, the outer webs 318a and 318b extend along the intermediate frame element 302a parallel to the longitudinal axis 317. In some implementations, the intermediate frame element 302a may be curved, and the main web 316 and the outer webs 318a and 318b may be formed such that the shapes of the main web 316 and the outer webs 318a and 318b correspond or conform to one another along the length 325. The intermediate frame element 302a also includes an overall width 335. The overall width 335 may be uniform along the length 325, as depicted in FIG. 6A, or may vary along the length 325.

FIG. 6A depicts a cutting plane line 610 and a cutting plane line 620. The cutting plane line 610 is disposed perpendicular to a longitudinal axis of the intermediate frame element 302a and passes through the center of the fastener through-hole 310. The cutting plane line 620, also disposed perpendicular to the longitudinal axis of the intermediate frame member 302a, passes through a portion of the intermediate frame element 302a that does not include a fastener through-hole 310. FIG. 6B illustrates a section view of the intermediate frame element 302a viewed orthogonally at the cutting plane line 610. FIG. 6C illustrates a section view of the intermediate frame element 302a viewed orthogonally at the cutting plane line 620.

FIG. 6B illustrates a cross-section of the intermediate frame element 302a. As depicted in FIG. 6B, the fastener through-hole 310 extends through the main web 316 from the first side 312 to the second side 314. In some implementations, the main web 316 and the fastener through-hole 310 may be configured to accommodate a fastener assembly 306.

The intermediate frame element 302a has the overall width 335 and an overall depth 345. In some implementations, the first plate 304a and the second plate 304b may be configured to abut exterior surfaces of the first side 312 and the second side 314, respectively. In some implementations, as shown in FIG. 6B, the first plate 304a and the second plate 304b may be received within a recess 320 such that the exterior surfaces 338 of the first and second plates 304a and 304b contact the exterior surfaces 305 of the intermediate frame element 302a defining the recess, including the main web 316. A recess 320 may be formed in one or both of the first side 312 and the second side 314. The recesses 320 may be sized to accommodate the first plate 304a and the second plate 304b. For example, the recesses 320 may be sized such that outer-most surfaces of the first plate 304a and the second plate 304b are flush with the exterior surfaces 340 of the intermediate frame element 302a.

As shown, the recesses 320 are formed in the outer webs 318a and 318b on both the first side 312 and the second side 314 of the intermediate frame element 302a. A depth of the main web 316 conforms to the recesses 320. Thus, as shown, a depth of the main web 316 is shortened to accommodate the first and second plates 304a and 304b. In still other implementations, a recess 320 may be formed in one of the first side 312 or the second side 314 but not in the other of the first side 312 or the second side 314.

In some implementations, at least one of the first plate 304a and the second plate 304b may have a thickness between 5% and 15% of the overall thickness 345 of the intermediate frame element 302a. In other instances, at least one of the first plate 304a and the second plate 304b may have a thickness less than 5% or greater than 15% of the overall thickness 345 of the intermediate frame element 302a. In implementations having one or more recesses 320, the recess or recesses 320 may be accordingly sized to accommodate the thickness of one or both of the first plate 304a and the second plate 304b.

FIG. 6C illustrates another cross-section of the intermediate frame element 302a. As shown, recesses 320 are formed in the outer webs 318a and 318b and the main web 316 on both of the first side 312 and the second side 314 of the intermediate frame element 302a. In some implementations, a width 322 of the main web 316 may be between 10% and 35% of the overall width 335 of the intermediate frame element 302a. In other implementations, the width of the main web 316 may be less than 10% of the overall width 335 of the intermediate frame element 302a or larger than 35% of the overall width 335 of the intermediate frame element 302a.

In some implementations, the width 322 of the main web 316 may be selected based on, for example, weight, strength, and rigidity considerations. In general, the strength, rigidity, and weight of the composite frame component 300 and the associated internal composite frame system 200 increases as the width 322 of the main web 316 increases. Likewise, in general, the strength, rigidity, and weight decreases as the width 322 of the main web 316 decreases. In some implementations, a width of the outer webs 318a and 318b may be selected to correspond with the width 322 of the main web 316. In other implementations, a width 322 of the main web 316 and a width of the outer webs 318a and 318b may be different from each other. In still other implementations, a cross-section of the intermediate frame element 302a may be solid such that the individual features of the main web 316 and outer webs 318a and 318b are not discernable.

Figure 7A:
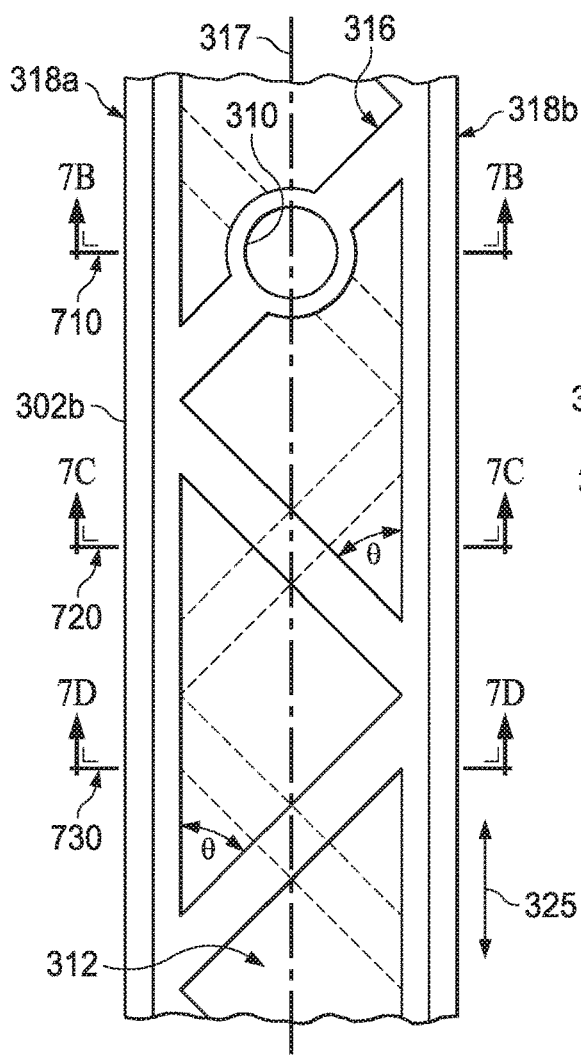
FIGS. 7A, 7B, 7C, and 7D are various detail and cross-sectional views of the example intermediate frame element depicted in FIG. 5.

FIGS. 7A, 7B, 7C, and 7D illustrate various detail and cross-sectional views of the intermediate frame element 302b depicted in FIG. 5. The intermediate frame element 302b differs from the intermediate frame element 302a in cross-sectional structure, but otherwise includes similar components. As shown in FIG. 7A, the main web 316 extends along a length of the intermediate frame element 302b in a zigzag pattern. Further, as also shown in FIG. 5, the zigzag pattern of the main web 316 on the first side 312 is opposite the zigzag pattern of the main web 316 on the second side 314. This opposite relationship is shown by the main web 316 show in solid lines, representing the arrangement of the main web 316 on the first side 312, for example, and the dotted line representing the arrangement of the main web 316 on the second side 314.

The cross-sectional shape of the intermediate frame element 302b provides improved torsional rigidity (as compared to the torsional rigidity provided by the intermediate frame element 302a). As a result, a composite frame component 300 incorporating the intermediate frame element 302b provides improved torsional rigidity. FIG. 7A illustrates a detail view of the first side 312 of the intermediate frame element 302b. The intermediate frame element 302b is depicted with the fastener through-hole 310, as described above with reference to FIGS. 3 and 5.

As depicted in FIG. 7A, the outer webs 318a and 318b extend parallel to one another and parallel to a longitudinal axis 317 of the intermediate frame element 302 along the length 325 thereof. In some implementations, the intermediate frame element 302b may be curved, and the outer webs 318a and 318b may corresponding shapes along the length 325. The main web 316 extends at an angle θ to the outer webs 318a and 318b. In some implementations, the main web 316 may extend at a larger or smaller angle than the angle θ depicted in FIG. 7A. As depicted in FIG. 7A and as explained above, the zigzag pattern of the main web 316 on the first side 312 is opposite the zigzag pattern of the main web 316 on the second side 314. As a result, the main web 316 forms a crossing pattern along the length 325 of the intermediate frame element 302b. However, the scope of the disclosure is not so limited. The main web 316 is intended to encompass other configurations including those in which the main web 316 extends along the length of the intermediate frame element in a mirroring pattern on both the first side 312 and the second side 314. For example, in some instances, an intermediate frame element may include a main web 316 that extends in a zigzag pattern on each side of the intermediate frame element and where the main webs 316 align or are mirror images of each other. In other implementations, on one or both of the first side 312 and the second side 314, the main web 316 may include offset zigzag patterns that combine to define a crisscross pattern.

Figure 7C:
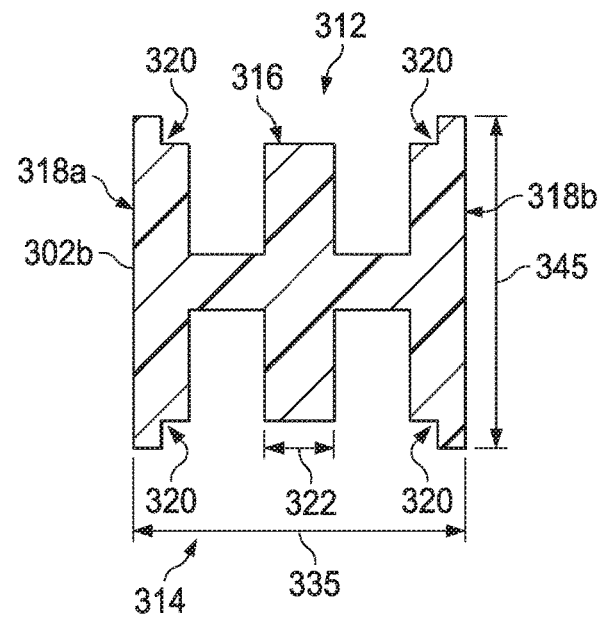
Figure 7B:
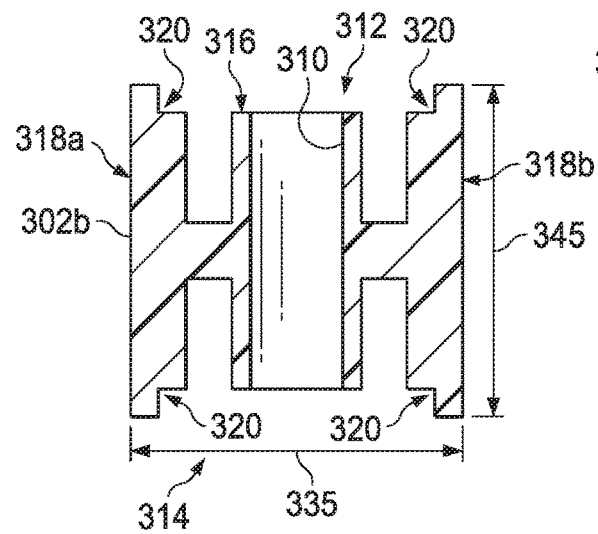
Figure 7D:
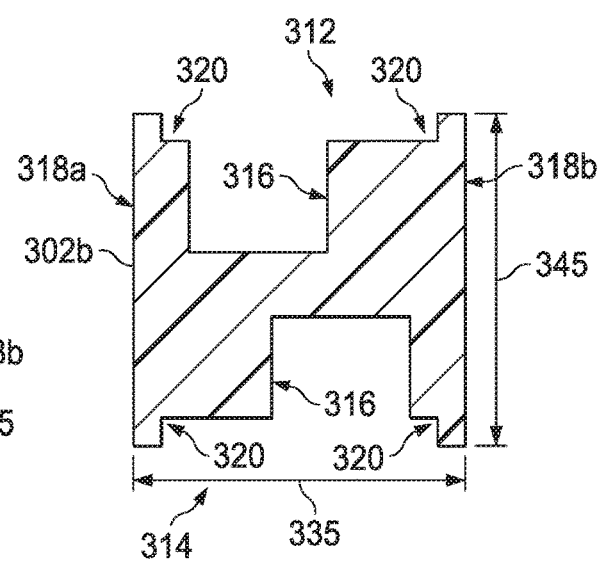

FIG. 7A depicts a cutting plane line 710, a cutting plane line 720, and a cutting plane line 730. The cutting plane line 710 is disposed perpendicular to a longitudinal axis of the intermediate frame element 302b and passes through a center of the fastener through-hole 310. The cutting plane line 720 is disposed perpendicular to a longitudinal axis of the intermediate frame element 302b and passes through a location away from a fastener through-hole 310 and where the main web 316 on each of the first side 312 and the second side 314 intersect when viewed from the side, as shown in FIG. 7A. The cutting plane line 730, also perpendicular to the longitudinal axis of the intermediate frame element 302b, passes through a location where the main web 316 intersects with the outer webs 318a and 318b. FIG. 7B illustrates a section view of the intermediate frame element 302b viewed orthogonally at the cutting plane line 710. FIG. 7C illustrates a section view of the intermediate frame element 302b viewed orthogonally at the cutting plane line 720. FIG. 7D illustrates a section view of the intermediate frame element 302b viewed orthogonally at the cutting plane line 730.

The intermediate frame element 302b shown in FIGS. 7B, 7C, and 7D include features similar to those shown in FIGS. 6B and 6C. Particularly, as shown in FIGS. 7B, 7C, and 7D, the intermediate frame element 302b includes recesses 320 that function similarly to those explained above with respect to the intermediate frame member 302a shown in FIGS. 6B and 6C. As such, the description of the recesses 320, as well as the other features similar to those shown in FIGS. 6B and 6C, are applicable here and will not be repeated.

FIGS. 8A, 8B, 8C, and 8D are each a cross-sectional view of an example composite frame component 300 that may be similar to those depicted in FIG. 2 and FIG. 3. Still further, a composite frame component that includes any of the types of intermediate frame elements described herein or otherwise encompassed by the present disclosure are also applicable. Each of the FIGS. 8A, 8B, 8C, and 8D includes an example fastener assembly 306. However, the scope of the disclosure is not so limited. The composite frame component 300 is intended to encompass other combinations of fasteners and fastener assemblies, for example, as described previously with respect to FIG. 3. The example composite frame component 300 is illustrated with the structural cross-member 350 integrally formed with the intermediate frame element 302. However, as explained above, the composite frame component 300 may be configured according to any of the examples described herein or as otherwise encompassed by the present disclosure. A portion of a remainder of the internal composite frame system 200, of which the illustrated composite frame component 300 forms a part, is also illustrated.

Figure 8A:
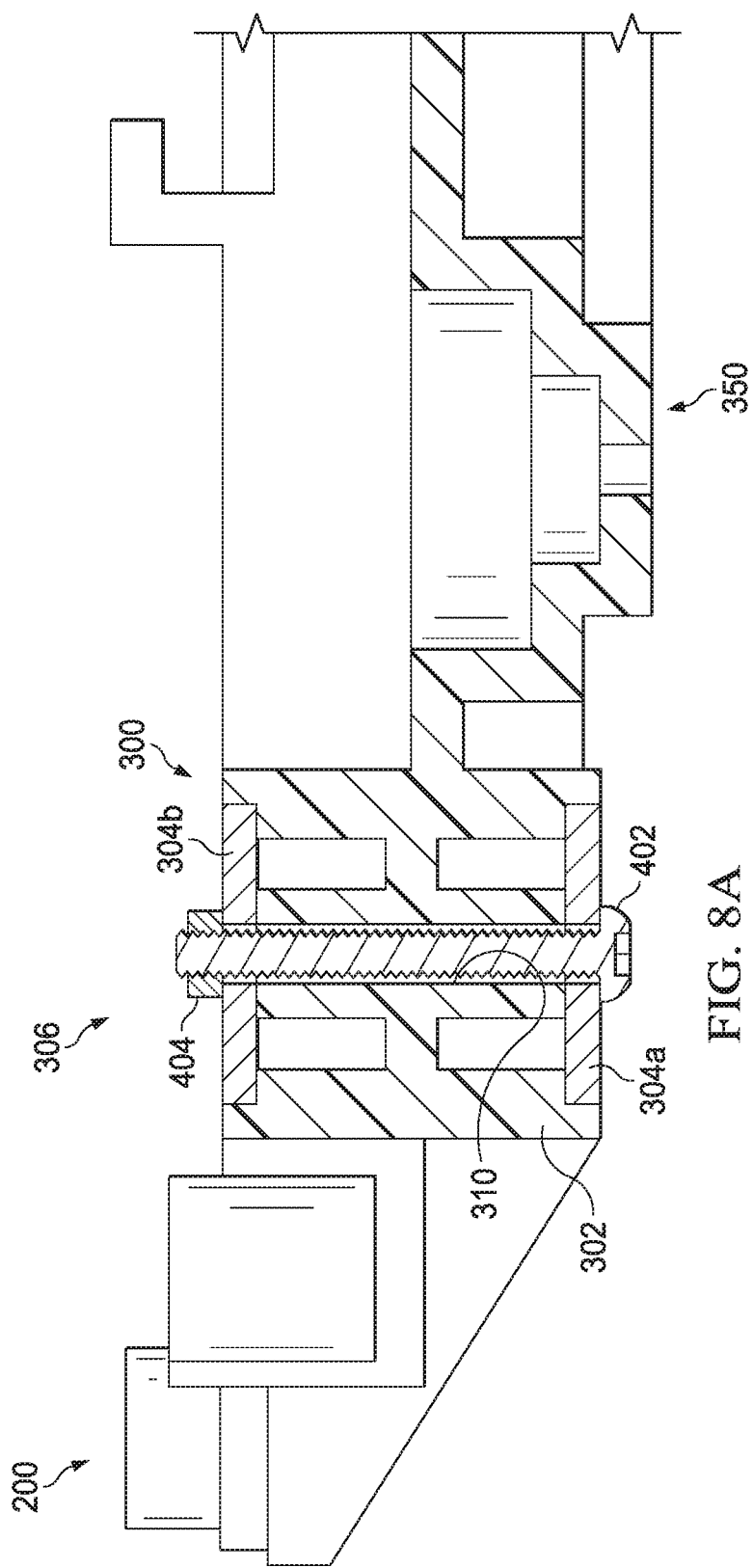

FIG. 8A illustrates the fastener assembly 306 with an example male fastener 402, e.g., a bolt or screw, and an example female fastener 404, e.g., a nut. The male fastener 402 is received into the fastener through-hole 310 and may be a button-head bolt, as depicted in FIG. 8A. The female fastener 404 may be a threaded nut, as depicted in FIG. 8A. In some instances, the nut may be welded onto or otherwise captured or secured to one of the first or second plates 304a and 304b. For example, in the context of the presently illustrated example, the female fastener 404 may be affixed to the second plate 304b.

Figure 8B:
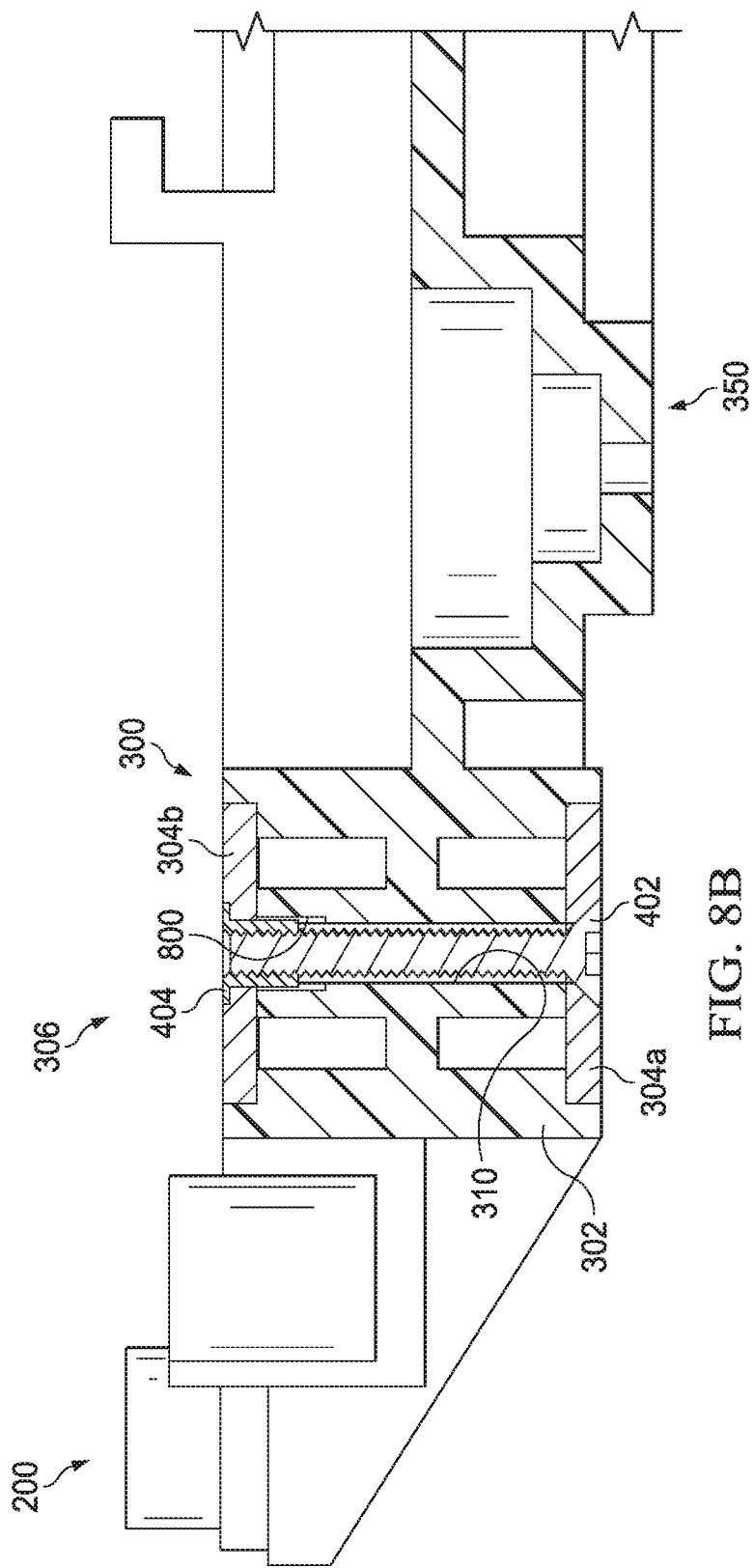

FIG. 8B illustrates another fastener assembly 306 in which an example male fastener 402, e.g., a bolt or screw, received within the fastener through-hole 310, engages the threaded surface of another example female fastener 404, e.g., a threaded sleeve or threaded clinch nut, to form a threaded engagement. The female fastener 404 may also be received within the fastener through-hole 310. The male fastener 402 may be a flat-head bolt, as depicted in FIG. 8B. The female fastener 404 may be a threaded clinch nut, as depicted in FIG. 8B. The female fastener 404 may be captured, affixed to, or otherwise secured to the second plate 304b. For example, the female fastener 404 may be coupled to the second plate 304b in such a way such that the second plate 304b prevents rotation of the female fastener 404 relative thereto. As show, the fastener through-hole 310 includes a radially enlarged portion 800 that receives the female fastener 404. In other implementations, the fastener through-hole 310 may have a constant cross-sectional size; the female fastener 404 may be received therein; and the size (e.g., diameter) of the male fastener 402 may be sized so as to be both receivable into the fastener through-hole 310 and receivable into the female fastener 404.

FIG. 8C illustrates an example fastener assembly 306 that includes a male fastener 402, e.g., a bolt or screw, and an example standoff 406. The standoff 406 includes a threaded bore 334 having a threaded internal surface 802 that matingly engages the exterior threaded surface of the male fastener 402. The male fastener 402 may be a button-head screw, as depicted in FIG. 8C. The standoff 406 may be a threaded clinch standoff, as depicted in FIG. 8C. The standoff 406 may be received into the second plate 304b such that an end surface of the standoff 406 and an exterior surface of the second plate 304b are flush. An opposing end surface of the standoff 406 abuts an inner-facing surface of the first plate 304a. In some implementations, the standoff 406 may be affixed to the second plate 304b or otherwise coupled thereto such that the standoff 406 is prevented from rotating relative to the second plate 304b. The standoff 406 extends through the fastener through-hole 310.

FIG. 8D illustrates yet another example fastener assembly 306 that includes two example male fasteners 402, e.g., bolts or screws, and an example standoff 406. The male fasteners 402 may be button-head bolts, as depicted in FIG. 8D. The standoff 406 may be a threaded standoff, as depicted in FIG. 8D. Particularly, the standoff 406 includes a threaded bore 334 that includes two separate threaded surfaces 806 and 808. Each of the threaded surfaces are configured to engage the external threaded surface of the male fasteners 402. In the illustrated example, opposing ends of the standoff 406 abut respective inner-facing surfaces of the first plate 304a and second plate 304b. The standoff 406 extends through the fastener through-hole 310.

In FIGS. 8A and 8B, the example fastener assemblies 306 extend through the first plate 304a, the intermediate frame element 302, and the second plate 304b. The male fastener 402 and the female fastener 404 engage each other to form a threaded connection. The male fastener 402 and the female fastener 404 may be tightened to cause the first plate 304a and the second plate 304b to be secured against the intermediate frame element 302, forming a composite assembly in which the intermediate frame element 302 is sandwiched between the first plate 304a and the second plate 304b. When tightened, the example fastener assemblies 306 depicted in FIGS. 8A and 8B exert a compressive force on the first plate 304a and the second plate 304b. The first plate 304a and the second plate 304b may also exert a portion of this compressive force on the intermediate frame element 302.

The example fastener assembly 306 shown in FIG. 8C includes the standoffs 406 that extends through the intermediate frame element 302 (via the fastener through-hole 310) and the second plate 304b but does not extend through the first plate 304a. In FIG. 8D, the standoff 406 extends through the intermediate frame element 302 (via the fastener through-hole 310) but does not extend through the first plate 304a or the second plate 304b. The male fastener 402 extends through one of the first plate 304a or the second plate 304b and the intermediate frame element 302. For example, in FIG. 8D, each of the male fasteners 402 passes through one of the first and second plates 304a and 304b and into the standoff 406 disposed in the fastener through-hole 310 formed in the intermediate frame element 302. The male fastener 402 and the standoff 406 may be threaded together and tightened against the first plate 304a and the second plate 304b when the composite frame component 300 is assembled.

When tightened, the example fastener assemblies 306 depicted in FIGS. 8C and 8D exert a compressive force on the first plate 304a and the second plate 304b. In some implementations, the standoff 406 may be designed such that the first plate 304a and the second plate 304b exert a portion of this compressive force on the standoff 406 rather than on the intermediate frame element 302. In other implementations, the standoff 406 may be designed such that the first plate 304a and the second plate 304b exert a portion of this compressive force on the intermediate frame element 302 rather than on the standoff 406.

The above-disclosed subject matter is to be considered illustrative, and not restrictive, and the appended claims are intended to cover all such modifications, enhancements, and other embodiments that fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A composite frame system comprising:
   at least one composite frame component comprising:
      an intermediate frame element comprising:
         a first side;
         a second side disposed opposite the first side;
         a main web; and
         at least two outer webs,
            wherein the main web extends parallel to the at least two outer webs along a length of the intermediate frame element;
      a first plate positioned on the first side of the intermediate frame element, wherein the first plate is in contact with at least one of the at least two outer webs on a first end of the first plate and in contact with at least one other of the at least two outer webs on an opposing second side of the first plate, wherein the first plate is further in contact with the main web between the first side and the second side of the first plate;
      a second plate positioned on the second side of the intermediate frame element wherein the second plate is in contact with at least one of the at least two outer webs on a first end of the second plate and in contact with at least one other of the at least two outer webs on an opposing second side of the second plate, wherein the second plate is further in contact with the main web between the first side and the second side of the second plate;
      wherein the first plate, the second plate and the at least two outer webs substantially enclose the main web along a length of the intermediate frame element; and
   at least one fastener assembly extending through the first plate, the intermediate frame element, and the second plate and attaching the first plate and the second plate to the intermediate frame element.

2. The composite frame system of claim 1,
   wherein the at least one outer web extends along a length of the intermediate frame element in an orientation parallel to a longitudinal axis of the intermediate frame element, and
   wherein at least a portion of the main web extends at an angle relative to the at least one outer web such that the main web forms a zigzag pattern along a length of the intermediate frame element.

3. The composite frame system of claim 1, wherein the intermediate frame element comprises:
   an overall width, wherein the main web comprises a width that is between 5% and 35% of the overall width.

4. The composite frame system of claim 1, wherein the intermediate frame element comprises an overall depth, and wherein the first plate and the second plate each have a thickness between 5% and 15% of the overall depth.

5. The composite frame system of claim 1, wherein the at least one fastener assembly comprises a male fastener and a female fastener.

6. The composite frame system of claim 1, wherein the at least one fastener assembly comprises at least one male fastener and a standoff.

7. The composite frame system of claim 1, wherein the at least one fastener assembly comprises a male fastener, a standoff, and a female fastener.

8. The composite frame system of claim 1, wherein the at least one fastener assembly applies a compressive force to the intermediate frame element, the first plate, and the second plate.

9. The composite frame system of claim 1 wherein a compressive force applied by the at least one fastener assembly is not transmitted through the intermediate frame element.

10. The composite frame system of claim 1, wherein the intermediate frame element is made from a first material, and wherein the first plate and the second plate are made from a second material different from the first material.

11. The composite frame system of claim 10 wherein the first material has a lower yield strength or a lower modulus of elasticity than the second material.

12. The composite frame system of claim 10 wherein the first material comprises a plastic, and wherein the second material comprises a metal.

13. The composite frame system of claim 1, further comprising at least one structural cross-member integrally formed with the intermediate frame element.

14. The composite frame system of claim 1, wherein the at least one fastener assembly comprises a plurality of fastener assemblies and wherein a distance separates adjacent fastener assemblies.

15. The composite frame system of claim 14, wherein the distance is between two inches and six inches.

16. The composite frame system of claim 1, wherein the at least two outer webs comprise opposing recesses that run along a length of the two outer webs and are configured to receive opposing sides of the first plate.

17. The composite frame system of claim 16, wherein the at least two outer webs comprise additional opposing recesses that run along the length of the two outer webs on the opposite side of the intermediate frame element and are configured to receive opposing sides of the second plate.

18. The composite frame of claim 17, wherein the first plate and the second plate are flush with outer edges of the at least two outer webs when received in their respective recesses.

* * * * *